(12) United States Patent
Rosenberg

(10) Patent No.: US 11,523,925 B2
(45) Date of Patent: *Dec. 13, 2022

(54) ELECTROPHYSIOLOGICALLY ACTIVE TRANSDUCER INTRAGASTRIC BALLOON SYSTEM AND METHOD

(71) Applicant: Proximate Concepts LLC, Fort Lee, NJ (US)

(72) Inventor: Paul Rosenberg, Saddle River, NJ (US)

(73) Assignee: Proximate Concepts LLC, Fort Lee, NJ (US)

( * ) Notice: Subject to any disclaimer, the term of this patent is extended or adjusted under 35 U.S.C. 154(b) by 488 days.

This patent is subject to a terminal disclaimer.

(21) Appl. No.: 16/747,085

(22) Filed: Jan. 20, 2020

(65) Prior Publication Data

US 2020/0155334 A1     May 21, 2020

Related U.S. Application Data

(63) Continuation of application No. 15/625,344, filed on Jun. 16, 2017, now Pat. No. 10,537,454.

(51) Int. Cl.
*A61F 5/00* (2006.01)
*A61N 7/00* (2006.01)

(52) U.S. Cl.
CPC ............ *A61F 5/0036* (2013.01); *A61F 5/003* (2013.01); *A61F 5/0026* (2013.01); *A61F 5/0083* (2013.01); *A61N 7/00* (2013.01); *A61F 5/0046* (2013.01); *A61N 2007/0026* (2013.01); *A61N 2007/0043* (2013.01)

(58) Field of Classification Search
CPC ...... A61F 5/0026; A61F 5/003; A61F 5/0036; A61F 5/0046; A61F 5/0083; A61N 2007/00; A61N 2007/0026; A61N 2007/0043
See application file for complete search history.

(56) References Cited

U.S. PATENT DOCUMENTS

| | | |
|---|---|---|
| 4,899,747 A | 2/1990 | Garren et al. |
| 5,084,061 A | 1/1992 | Gau et al. |
| 6,755,869 B2 | 6/2004 | Geitz |
| 6,826,428 B1 | 11/2004 | Chen et al. |
| 8,062,207 B2 | 11/2011 | Gannoe et al. |
| 8,092,482 B2 | 1/2012 | Gannoe et al. |
| 8,226,602 B2 | 7/2012 | Quijana et al. |
| 8,870,907 B2 | 10/2014 | Gaur et al. |
| 8,974,483 B2 | 3/2015 | Gaur et al. |

(Continued)

*Primary Examiner* — Phong Son H Dang
(74) *Attorney, Agent, or Firm* — Leason Ellis LLP

(57) ABSTRACT

Systems and methods for treating eating disorders using electro-physiologically active transducer intragastric balloon system ("EAT system") are described herein. The EAT System includes an intragastric balloon that is configured to operate in a typical fashion and further modified to include an integrated electro-physiological stimulation unit. The stimulation unit is configured to generate impulses using a transducer that are suitable for stimulating sensory receptors located around the stomach. In particular, transducer transmits mechanical waves through the fluid within the IG balloon and its outer shell to any receptors of the vagus nerve system that are located in the vicinity of the IG balloon. Controlled stimulation of the vagus nerve fibers using the stimulation unit can effectively produce appetite controlling sensations of satiety beyond the typical efficacy period of an unmodified IG balloon.

3 Claims, 9 Drawing Sheets

(56) References Cited

U.S. PATENT DOCUMENTS

| | | |
|---|---|---|
| 9,668,901 B2 | 6/2017 | Dominguez et al. |
| 9,962,276 B2 | 5/2018 | Quijano et al. |
| 10,182,932 B2 | 1/2019 | Moss et al. |
| 2002/0055757 A1 | 5/2002 | Torre et al. |
| 2003/0158569 A1 | 8/2003 | Wazne |
| 2003/0171768 A1 | 9/2003 | McGahn |
| 2004/0267378 A1 | 12/2004 | Gazi et al. |
| 2005/0245957 A1 | 11/2005 | Starkebaum et al. |
| 2007/0016262 A1 | 1/2007 | Gross et al. |
| 2007/0100368 A1 | 5/2007 | Quijano et al. |
| 2007/0100369 A1 | 5/2007 | Cragg et al. |
| 2007/0149994 A1 | 6/2007 | Sosnowski et al. |
| 2008/0097513 A1 | 4/2008 | Kaji et al. |
| 2008/0147002 A1 | 6/2008 | Gertner |
| 2008/0208241 A1 | 8/2008 | Weiner et al. |
| 2008/0241094 A1 | 10/2008 | Burnett et al. |
| 2008/0243071 A1 | 10/2008 | Quijano et al. |
| 2008/0243166 A1 | 10/2008 | Paganon et al. |
| 2008/0243167 A1 | 10/2008 | Paganon et al. |
| 2008/0269555 A1 | 10/2008 | Paganon et al. |
| 2009/0093838 A1 | 4/2009 | Paganon |
| 2009/0131968 A1 | 5/2009 | Birk |
| 2009/0149879 A1 | 6/2009 | Dillon |
| 2009/0192535 A1 | 7/2009 | Kasic, II |
| 2010/0191270 A1 | 7/2010 | Garza Alvarez |
| 2011/0307075 A1 | 12/2011 | Sharma |
| 2012/0004676 A1 | 1/2012 | Vargas |
| 2012/0089169 A1 | 4/2012 | Werneth et al. |
| 2012/0095385 A1 | 4/2012 | Dominguez et al. |
| 2012/0116182 A1 | 5/2012 | Wong et al. |
| 2012/0191123 A1 | 7/2012 | Brister et al. |
| 2012/0232361 A1 | 9/2012 | Birk |
| 2012/0245553 A1 | 9/2012 | Raven et al. |
| 2012/0289992 A1 | 11/2012 | Quijano et al. |
| 2013/0035711 A1 | 2/2013 | Schwab et al. |
| 2013/0211440 A1 | 8/2013 | Schwab et al. |
| 2013/0267983 A1 | 10/2013 | Pavlocic et al. |
| 2013/0267984 A1 | 10/2013 | Gaur et al. |
| 2013/0289604 A1 | 10/2013 | Brister et al. |
| 2014/0288535 A1 | 9/2014 | Raven et al. |
| 2015/0196408 A1 | 7/2015 | Moss et al. |
| 2015/0209169 A1 | 7/2015 | Babkes et al. |
| 2015/0216697 A1 | 8/2015 | Kierath |
| 2015/0230956 A1 | 8/2015 | Sobelman et al. |
| 2016/0095731 A1 | 4/2016 | Connor |
| 2017/0172778 A1 | 6/2017 | Brister et al. |

ELECTROPHYSIOLOGICALLY ACTIVE TRANSDUCER INTRAGASTRIC BALLOON SYSTEM AND METHOD

CROSS-REFERENCE TO PRIOR APPLICATION

This application is a continuation of, and claims priority from, U.S. patent application Ser. No. 15/625,344, titled ELECTROPHYSIOLOGICALLY ACTIVE TRANSDUCER INTRAGASTRIC BALLOON SYSTEM AND METHOD, filed Jun. 16, 2017, which is hereby incorporated by reference in its entirety.

FIELD OF THE INVENTION

The invention relates to medical devices and more specifically, devices and methods for treatment of obesity using intragastric balloons.

BACKGROUND

The present invention relates generally to methods and apparatus for treating eating disorders using intragastric ("IG") balloons, and more particularly to techniques for treating patients with overeating disorders, especially obese patients, by using an IG balloon having an integrated electrophysiologically active transducer system. An integrated electrophysiologically active transducer allows for the generation of a range of acoustic waveforms within the saline solution that fills the balloon and propagates to the sidewalls of the balloon. Such waveform propagation amplifies and modulates the stimulus to the satiety receptors lying within the wall of the stomach, sending afferent signals through the vagus nerve to the brain and thereby diminishing hunger, as well as furnishing the central nervous system with a general sense of wellness, contentment and satiety.

Obesity is a serious and widespread health problem facing the world today. Classic treatment options for obese people include nutritional counseling, dieting and exercise. Such treatments, however, have demonstrated relatively poor long-term success rates. Surgical procedures including gastric restriction in cases of severe obesity have shown some success, although such procedures necessitate major surgery and have high morbidity and mortality rates.

IG balloons are a known treatment alternative to the more commonly known options such as bariatric surgery, diet suppression medication, psychotherapy, physical exercise and surgery. Generally, the practice involves placing a deflated IG balloon into the stomach of a patient and then expanding the IG balloon by instillation of saline solution or a relatively inert gas such as nitrogen, thus effectively reducing the available area within the stomach and limiting capacity for food through its space occupying presence in the lumen of the stomach.

Existing IG balloons are typically single balloons, but may be multiple in number. Their shape may be spherical, cylindrical or pear shaped, the final fill volume generally ranges from 200-700 ml. Generally, the outer shell of the balloon is constructed from an elastomer such as silicone or polyurethane. Expansion of the IG balloon is achieved through instillation of physiologic saline or a relatively inert gas via a fill tube which extends from the balloon itself up the esophagus and exits the mouth. Once the balloon has been fully expanded, the fill tube is disengaged from the balloon by application of pressure on the fill tube, which separates the tube from the balloon at a specially designed port location on the wall of the balloon. As noted, IG balloons are inserted into the stomach in a deflated state using an endoscope to perform a pre-deployment evaluation of the integrity of the esophageal mucosal, its anatomy and that of the stomach as well. The balloon is then inflated by syringe or pump injection of a predetermined volume of saline or by pressurized instillation of an inert gas, e.g., nitrogen.

As noted, gastric distension caused by the balloon as well as by the presence of food stimulates various neuroreceptors located in the stomach wall and causes the patient to experience a feeling of fullness during the experience of food consumption. Continued use of the balloon typically results in a decrease in the daily caloric intake by the patient and subsequently a loss in body weight. Though quite effective in assisting in weight loss, a well recognized finding is that of a diminishing return with the passage of time. For reasons not fully understood, the effectiveness of IG balloons in appetite suppression seems to decline in many patients after approximately six (6) months. For this reason, it is commonly recommended that IG balloons be defeated and removed after that general time period, with the possibility of reinsertion at a later time.

Additional approaches for treating obesity include implanting prosthetics within the stomach wall that bias the stretch receptors in the stomach by pre-stretching and thereby inducing an early sensation of satiety, for instance, as described in US Pat. Pub. No. 2005/0245957 to Starkebaum, et al. As would be understood in the art, "stretch receptors" located within the wall of the stomach are coupled to the central nervous system via the afferent (going away from the stomach and towards the brain) and efferent fibers (sending impulses away from the brain towards the stomach and digestive tract) of the vagus nerve, also known as the 12th Cranial Nerve or CNXII.

There also exist systems for treatment of obesity that selectively apply modulating electrical signals to the patient's vagus nerve. Modulating signals may be used to stimulate vagal activity to increase the flow of neural impulses up the nerve, or to inhibit vagal activity to block neural impulses from moving up the nerve, toward the brain, for producing excitatory or inhibitory neurotransmitter release. Such vagus nerve stimulation systems require a stimulus generator and leads having a nerve electrode implanted within the patient's body, in particular, on the vagus nerve or a branch thereof. In use, the stimulus generator is triggered to apply stimulation to the vagus nerve system.

Vagal nerve blockade devices require invasive surgery and general anesthesia, each with its associated elevated risk in obese patients. These procedures are also very expensive and are not covered by medical insurance. Research studies have proven the efficacy of implantable vagus nerve stimulators in weight loss and in the control of Type II diabetes mellitus, a life-threatening condition brought on by obesity, but the invasiveness of the treatment as well as the cost are disincentives to its common use. As can be appreciated, neurostimulators including implanted electrical leads placed around the trunk of the Vagus nerve in the chest or neck as the nerve makes its way to or from the brain, is an invasive solution which is not selective and may be associated with unintended or undesirable sequella including gastric paresis, delayed intestinal transit time, bloating and distension, wound infection, complications associated with anesthesia and complications associated with airway management in the morbidly obese.

By way of background, the vagus nerve is the dominant nerve of the gastrointestinal ("GI") tract and includes right and left branches connecting the GI tract to the brain. The vagus nerve generously innervates many, if not most of the organs associated with digestion, including, but not limited to, the distal esophagus, the stomach, the large and small intestines, the gall bladder, the pancreas and others. In the lower part of the chest, the left vagus rotates, becomes the anterior vagus, and innervates the stomach. The right vagus rotates to become the posterior vagus, which branches into the celiac division and innervates the duodenum and proximal intestinal tract.

Satiety signals include the stretch of mechanoreceptors, and the stimulation of certain chemosensors. The exact mechanisms leading an individual to satiety are not fully known, but a substantial amount of information has been accumulated.

It is with respect to these and other considerations that the disclosure made herein is presented.

SUMMARY

According to one embodiment an electro-physiologically active for treating obesity is disclosed, which may be embedded within an intragastric balloon device. The device according to one embodiment comprises an intragastric balloon (IG balloon) having a shell surrounding an internal volume for containing a fluid medium therein. The IG balloon is configured to be deployed into a patient's stomach during treatment. The device further comprising a stimulation unit that is integrated into the IG balloon. In particular, the stimulation unit comprises a transducer that is configured to transmit a stimulation signal through the fluid, wherein the signal is suitable for transmission through the fluid and stimulating one or more sensory receptors in the stomach. In another embodiment, a portion of the emitter extends beyond the wall of the silicone elastomer shell of the balloon and is operative to emit direct electrical or other stimulation to the stomach wall.

According to one embodiment an electro-physiologically active transducer is provided in conjunction with an intragastric balloon device for treating obesity is disclosed. In particular, the system comprises an intragastric balloon (IG balloon) having a shell surrounding an internal volume for containing a fluid medium therein. The IG balloon is configured to be deployed into the patient's stomach during treatment. The system also includes a stimulation unit that is integrated into the IG balloon or may be free-floating within the lumen of the balloon itself.

The stimulation unit according to one embodiment comprises a processor, a power supply, and a transducer that is electronically coupled to the processor. The transducer is under the control of the processor, and can transmit a stimulation signal through the fluid and the balloon shell, wherein the signal is suitable for stimulating one or more sensory receptors in the stomach. The stimulation unit may further comprise a wireless communication interface configured to establish a wireless electronic communication connection between the processor and an external computing device, which may comprise a patient application that is executable on the external computing device. In particular, the patient application configures the external computing device to transmit operational instructions to the processor over the wireless communication connection. Accordingly, the processor generates the signal using the transducer according to the received command instructions.

Various features, aspects and advantages of the invention can be appreciated from the following Description of Certain Embodiments and the accompanying Drawing Figures.

DESCRIPTION OF THE DRAWING FIGURES

Figure 2:
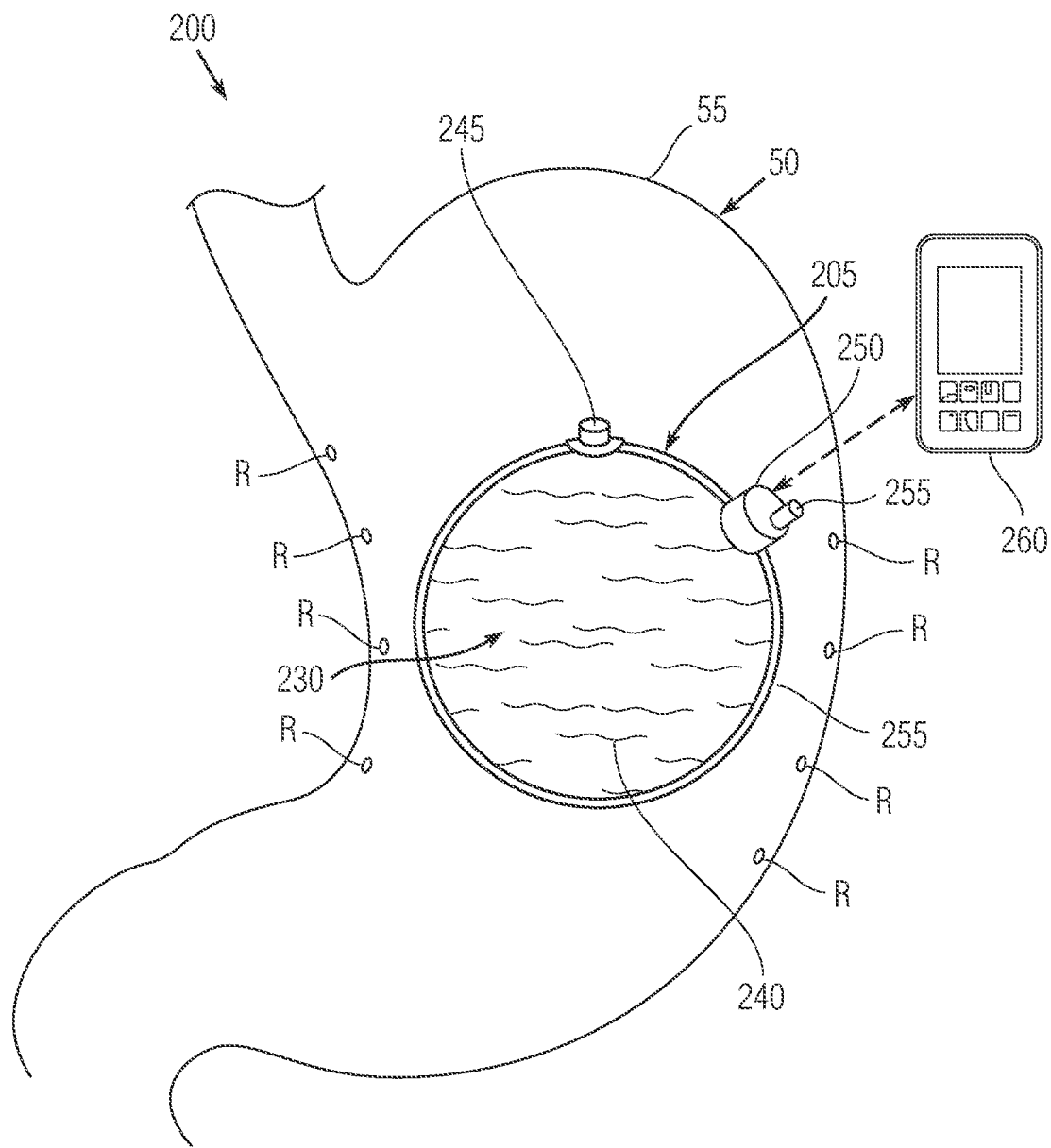
FIG. 2 is a high level diagram illustrating electro-physiologically active transducer intragastric balloon system in an operative state according to one or more embodiments of the invention.
Figure 10:
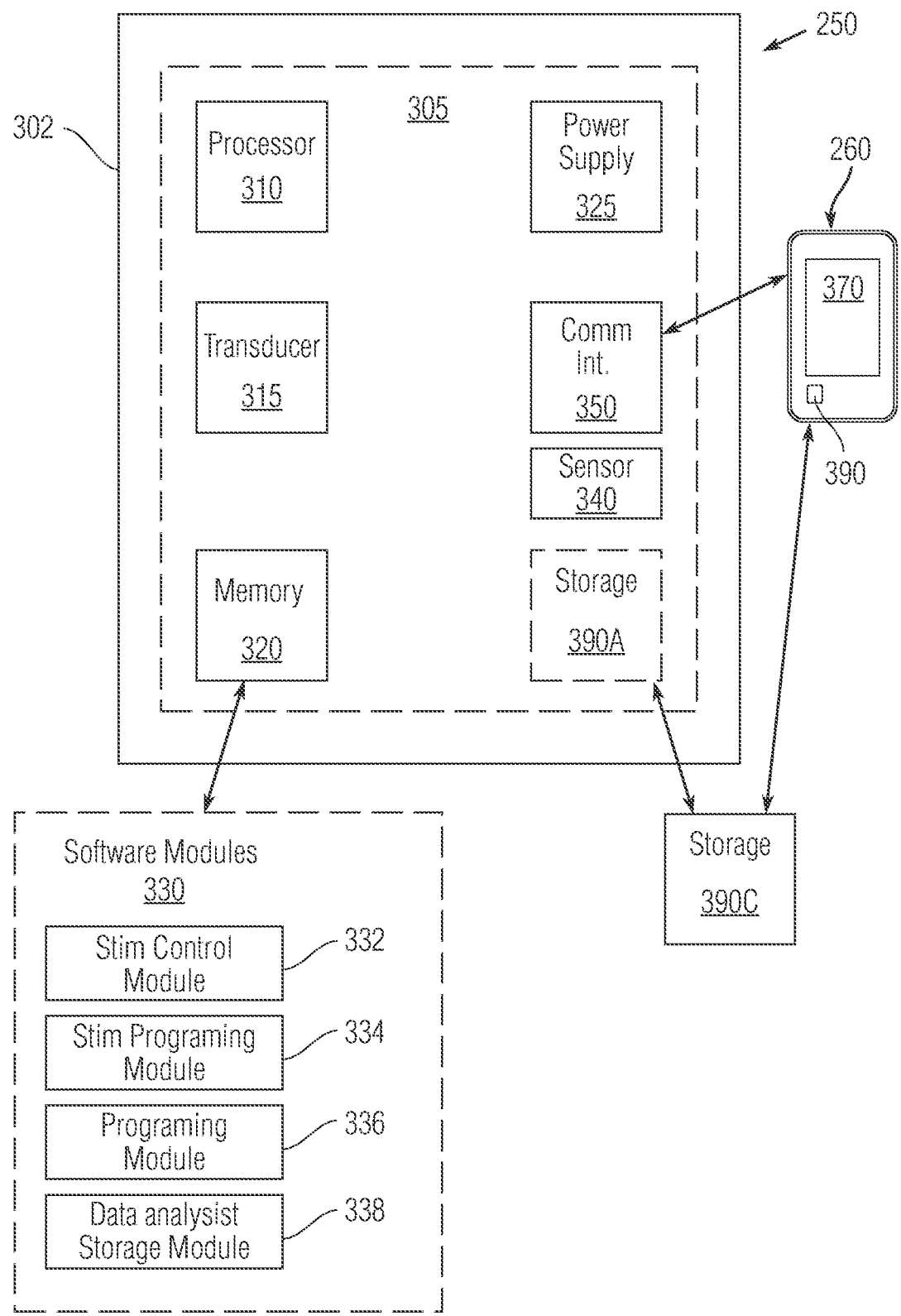
Figure 11:
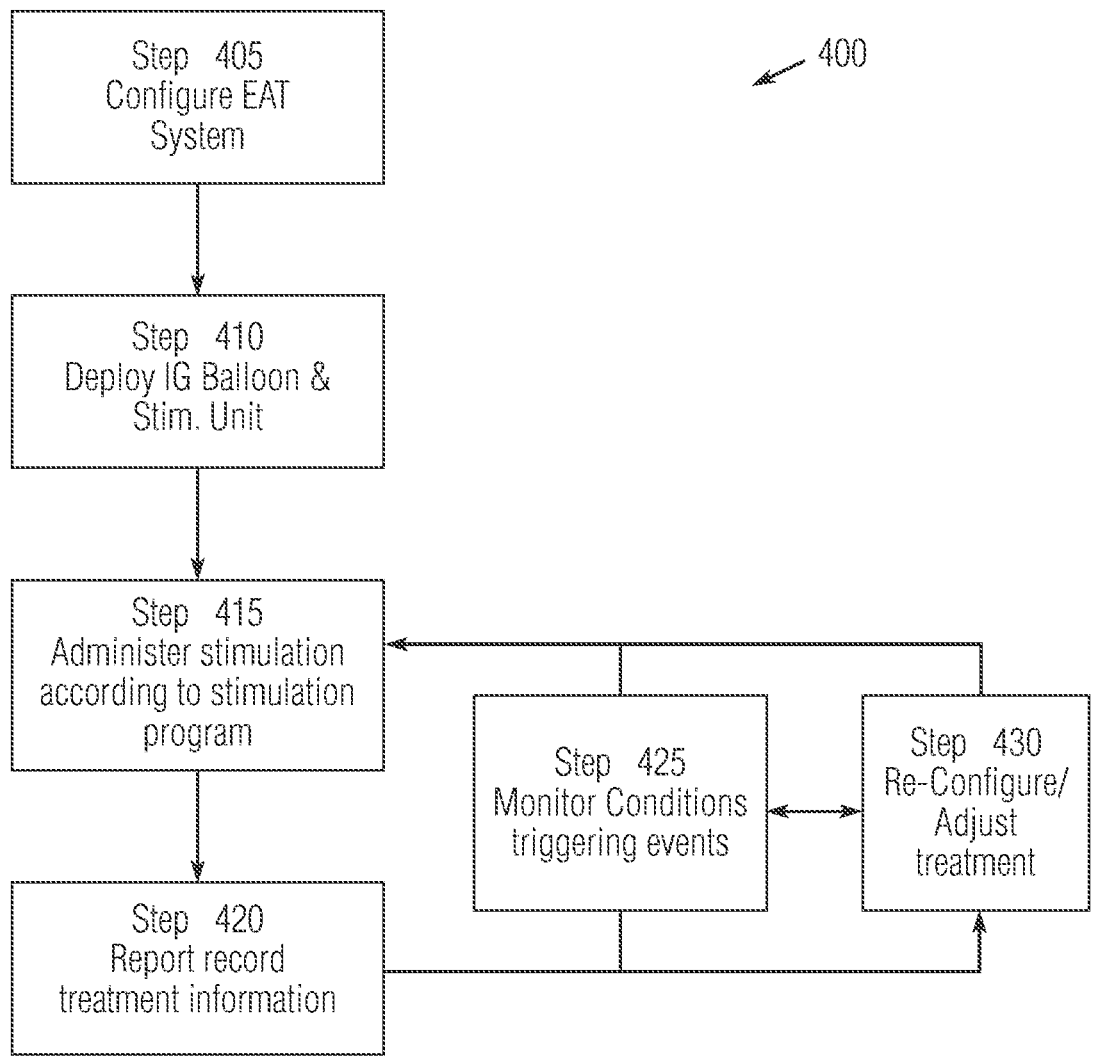

FIG. 10 is a conceptual diagram illustrating an exemplary stimulation unit of the electro-physiologically active transducer intragastric balloon system of FIG. 2 according to one or more embodiments of the invention; and FIG. 11 is a flow diagram illustrating an exemplary routine for administering treatment using the electro-physiologically active transducer intragastric balloon system of FIG. 2 according to one or more embodiments of the invention.

DETAILED DESCRIPTION OF CERTAIN EMBODIMENTS

By way of overview and introduction, systems and methods for treating eating disorders including obesity using electro-physiologically active transducer intragastric balloon system are described herein. In particular, the exemplary electro-physiologically active transducer intragastric balloon systems disclosed herein include an intragastric balloon component having an integrated electro-physiological stimulation unit. Generally, the IG balloon component is constructed and configured to operate in a similar fashion to IG balloon systems that are known in the art and commercially available (e.g., IG balloon systems marketed under the brand names ORBERA™, RE-SHAPE™, ELIPSE™ and OBALON™) According to a salient aspect, the IG balloon component is modified to include a stimulation unit that is configured to generate impulses suitable for stimulating any number of different sensory receptors of the stomach, including afferent and efferent fibers of the vagus nerve system located around the stomach. Accordingly, rather than stimulating the trunk/branches of the vagus nerve, the disclosed systems are configured to stimulate the receptors located within the wall of the stomach, which can include efferent and afferent fibers (input or inwardly conducting) to the vagus nerve.

More specifically, in some embodiments, the improved IG balloon can be configured to add to its physical presence alone, as perceived by a patient's stomach, and increase the measure of its electro-physiologic action by selectively transferring stimulating signals (i.e., transmitting energy in the form of mechanical waves or impulses) into the medium contained within the balloon, for instance, a saline solution. The stimulation, for example, can create mechanical waves that can be transmitted by and through the fluid of the balloon and through the outer shell to any receptors of the vagus nerve system that are located in the vicinity of the IG balloon. More stimulation of the fibers of the vagus nerve can be beneficial in achieving the transmission of a sustained pleasure response to the central nervous system via the vagus nerve. This effect can be extended beyond the period of efficacy of a typical unmodified IG balloon. As a result, the effectiveness of the IG balloon device can be increased and its usefulness in the treatment of obesity can be prolonged beyond the effective life of a typical, unmodified IG balloon.

Figure 1A:
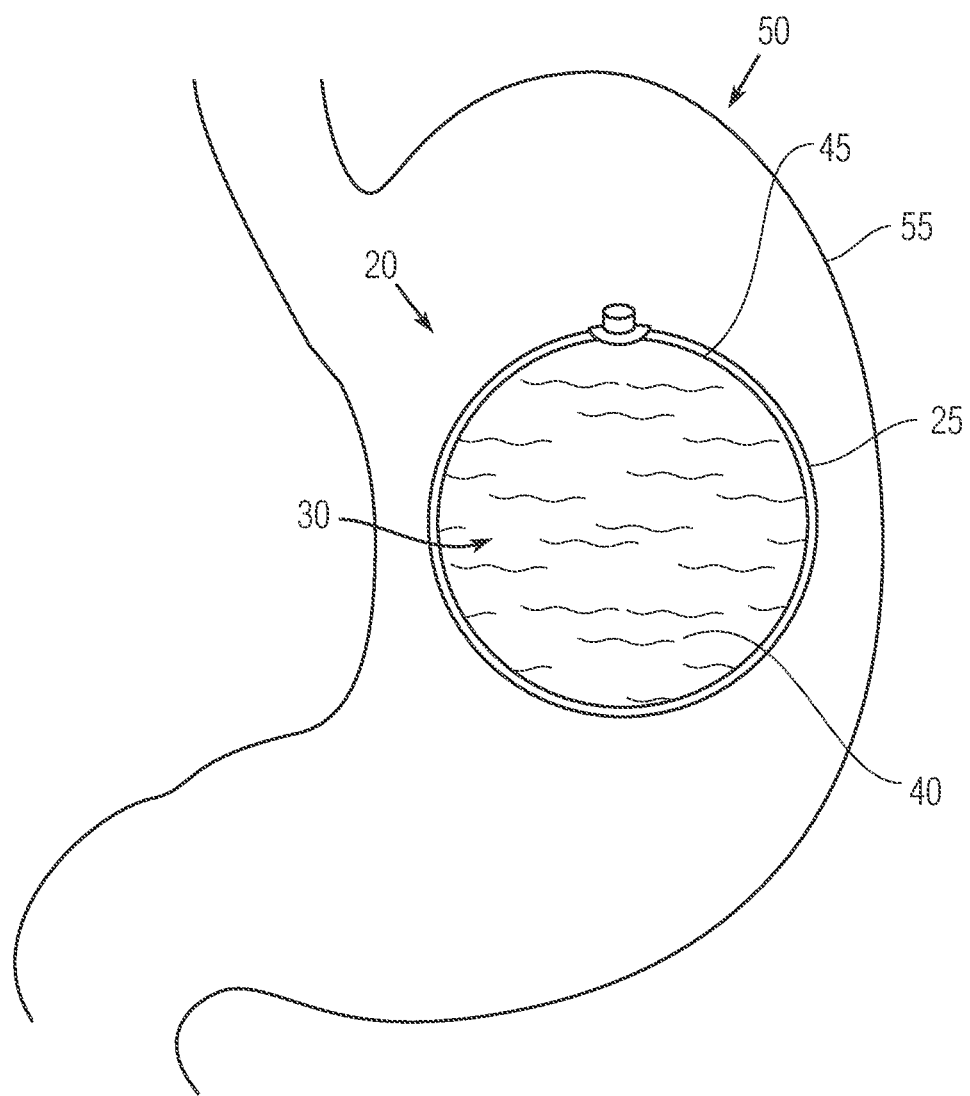
FIG. 1A is a high-level diagram of an exemplary intragastric balloon as known in the prior art.

Referring now to the drawing Figures and particularly to the perspective view of FIG. 1A, an exemplary intragastric balloon 20 as known in the prior art is shown in an expanded/operative state in a patient's stomach. IG balloons, such as balloon 20, can typically be spherical, cylindrical, ellipsoid or pear shaped, and can range in size from 200-700 ml or more, although alternative shapes and sizes are possible as well. The balloon can be made of an elastomer shell 25 such as silicone, polyurethane, or latex (rarely used due to complications that arise from its allergic potential), which defines and surrounds an internal cavity 30.

Figure 1B:
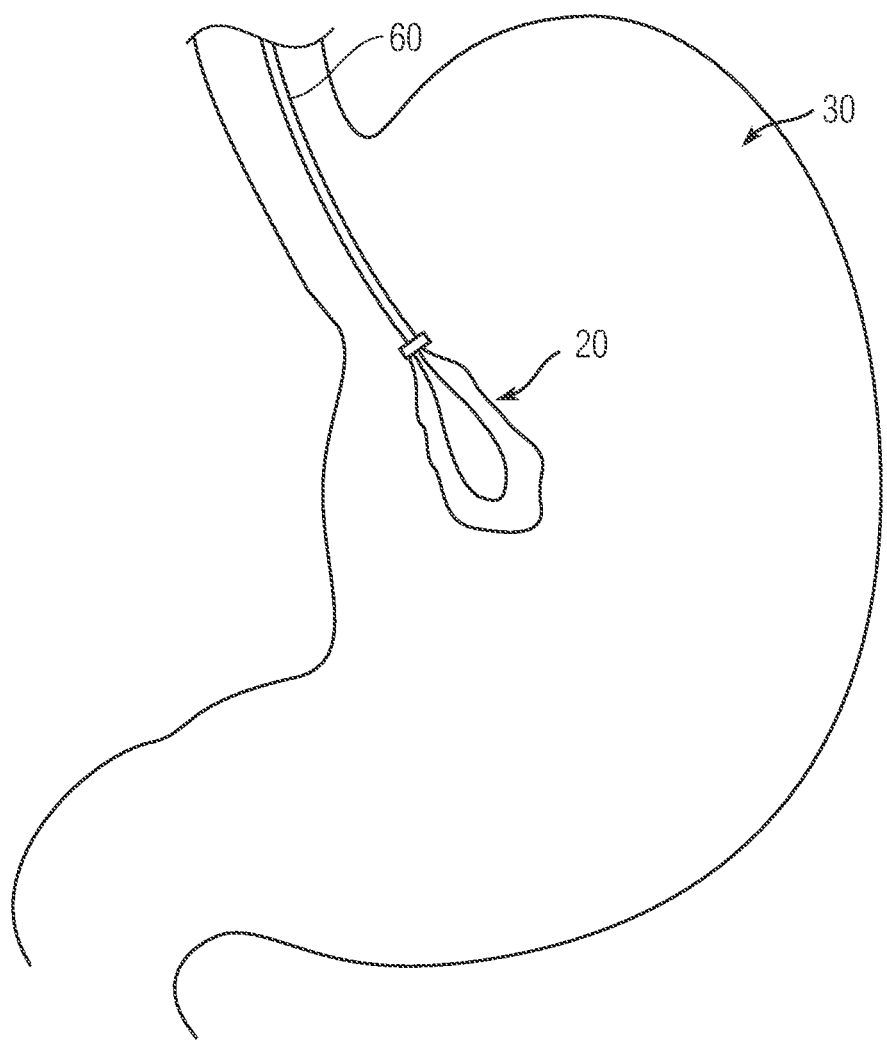
FIG. 1B is a high level diagram illustrating the intragastric balloon of FIG. 1 in a collapsed state during deployment into a patient's stomach.

As illustrated in FIG. 1B, the IG balloon 20 can be inserted into the patient's stomach 50 in a deflated state using an endoscope (not shown) and can then be inflated by filling the balloon's interior volume with a gaseous or liquid medium using a tube 60. The tube 60 typically passes through the patient's mouth and esophagus and is attached to the balloon before and during deployment. Returning to FIG. 1A, balloon 20 can also include a valve 45 that is suitable for allowing the inflow of the liquid or gaseous medium into the balloon cavity and, thereafter, seal the medium within the internal cavity so as to maintain the balloon in an expanded state and prevent leakage of the medium from the cavity. The purpose of the valve is also to permit deflation of the balloon before removal from the stomach. By example and without limitation, the valve 45 can be a one-way and self-sealing valve or other suitable temporary or permanent valve for selectively permitting the inflow and out-flow of the liquid or gaseous medium, as well as sealing the balloon during use, as would be understood in the art.

IG balloons can be free-floating within the cavity of the stomach 50, however, an IG balloon can be configured for deployment such that it remains in a specific position relative to the wall 55 of the stomach. It should be understood that other IG balloon configurations and methods for deploying and inflating such balloons exist.

Whereas the mere concept of using IG balloons for weight reduction is not new, the improved IG balloon device that is incorporated into the EAT system as further described herein in connection with FIGS. 2 through 11 have several novel features that result in improved efficacy and a longer effective life relative to existing IG balloon systems. For simplicity, the exemplary improved IG balloon device configurations that are further described herein in connection with FIGS. 2 through 11 are described as being based on a basic IG balloon. It should be understood, however, that the disclosed embodiments can be incorporated with any number of different types of IG balloon systems that are currently known and realized in the future without departing from the scope of the disclosed invention. Accordingly, certain features relating to the improved IG balloon component of the EAT system are further described herein in detail, whereas standard features of known IG balloons are described only to the extent considered necessary to explain and emphasize the novel features.

FIG. 2 is a high-level perspective view of an exemplary electro-physiologically active transducer intragastric balloon system 200 (an "EAT system") according to one or more embodiments of the invention. FIG. 2 illustrates an exemplary improved IG balloon component 205 of the EAT system deployed within the patient's stomach 50 in an expanded and operative state. As shown in FIG. 2, the improved IG balloon 205 includes a flexible shell 225, which surrounds an internal cavity 230. The IG balloon 205 also includes a valve 245 that is suitable for allowing the inflow of the medium 240 into the balloon's cavity and, thereafter, sealing the medium within the internal cavity during use. By way of example and without limitation, the medium 240 used to fill the cavity can be a fluid, for instance, a saline solution.

According to a salient aspect, as shown in FIG. 2, the EAT system 200 includes a stimulation unit 250 that is integrated with the balloon 205. In general, and as further described below, embodiments of the stimulation unit 250 can include various electronic components such as a processor and a transducer that are configured to implement stimulation regimens for the treatment of obesity by controllably generating impulses that are suitable for stimulating nearby sensory receptors of the stomach, which are identified by the reference "R" in FIG. 2A. In addition, the stimulation unit 250 can also be configured to communicate wirelessly with one or more external computing devices, such as a mobile device 260 of a patient. In addition, the stimulation unit 250 may be powered by an internal power source that may be inductively charged through a number of transcutaneous methods, including, but not limited to, an inductive coupler placed on the skin surface that emits electromagnetic radiation. A successful link with an inductive coupler may be indicated by a sound, light or haptic signal to the user that the coupling has taken place and that the power source is charging. It should further be noted that the coupling display according to certain embodiments can indicate percent of power source charged and time to full power source charge, which can be presented on the mobile device 260. Accordingly, implementation of a stimulation regimen for treating obesity can be coordinated, monitored and adjusted using either the stimulation unit 250, the mobile device 260 or a combination of the foregoing.

Figure 3:
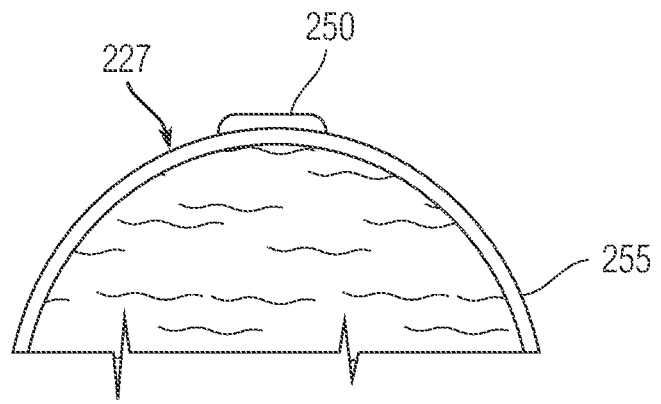
FIG. 3 is a high level diagram illustrating an exemplary configuration of an intragastric balloon device of the electro-physiologically active transducer intragastric balloon system of FIG. 2 according to one or more embodiments of the invention.
Figure 4:
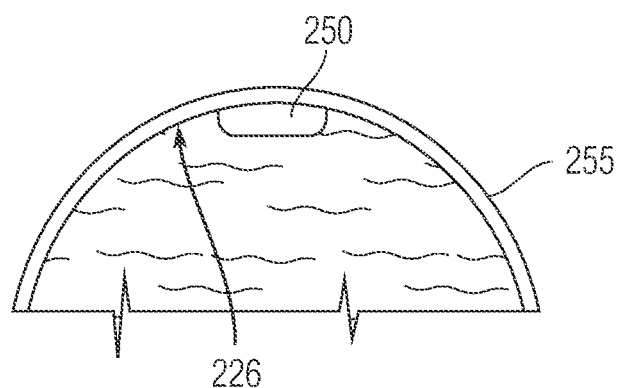
FIG. 4 is a high level diagram illustrating an exemplary configuration of an intragastric balloon device of the electro-physiologically active transducer intragastric balloon system of FIG. 2 according to one or more embodiments of the invention.
Figure 5:
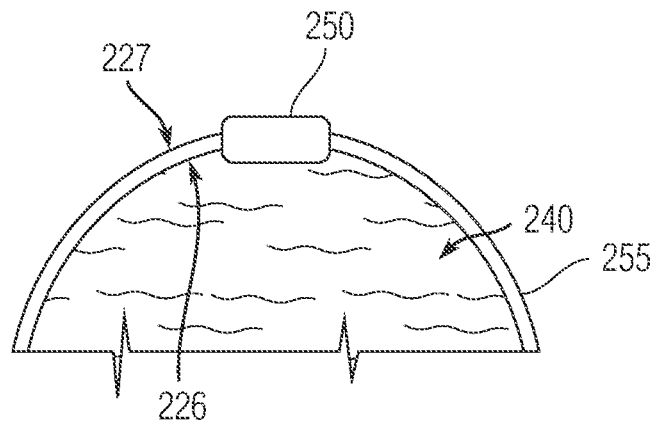
FIG. 5 is a high level diagram illustrating an exemplary configuration of an intragastric balloon device of the electro-physiologically active transducer intragastric balloon system of FIG. 2 according to one or more embodiments of the invention.

In some implementations, as shown in FIG. 3, which is a cut-away side-view of an exemplary configuration of IG balloon 205 in accordance with one or more of the disclosed embodiments, the stimulation unit 250 can be coupled to the exterior surface or shell 225 of the balloon, for instance, by fixedly or detachably mounting the stimulation unit to an exterior surface using any suitable temporary or permanent mounting device. In addition or alternatively, as shown in FIG. 4, which is a cut-away side-view of the IG balloon 200 shell in accordance with one or more of the disclosed embodiments, a stimulation unit can be similarly coupled to an interior surface or shell 225 of the balloon such that it is primarily disposed within the cavity 230 of the balloon. In addition or alternatively, as shown in FIG. 5, which is a cut-away side-view of the IG balloon 200 shell in accordance with one or more of the disclosed embodiments, a stimulation unit 250 can be integrated into the shell 225 such that it extends through all or part of the thickness of the shell. In such a configuration a side of the stimulation generator 250 can be directly exposed to the medium through the internal surface 226 of the shell, for instance, to facilitate transmission of the stimulation signals directly into the medium 240. In addition or alternatively, a side of the stimulation unit 250 can also be exposed through an external surface 227 of the shell, for instance, to facilitate inductive charging of the power supply, as further described herein.

Figure 6:
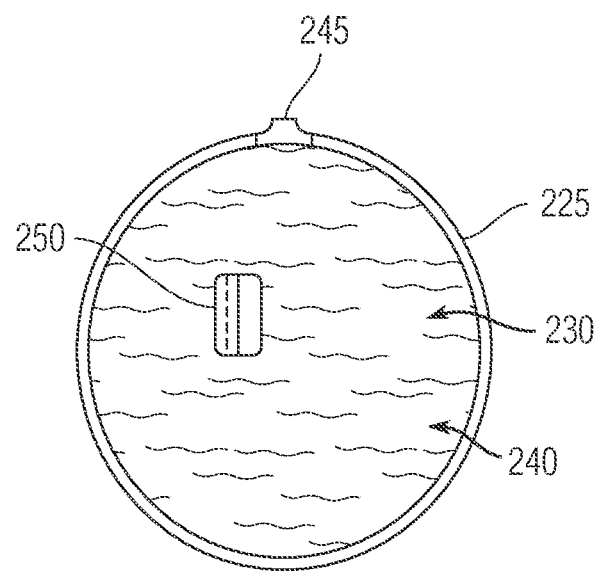
FIG. 6 is a high level diagram illustrating an exemplary configuration of an intragastric balloon device of the electro-physiologically active transducer intragastric balloon system of FIG. 2 according to one or more embodiments of the invention.
Figure 7:
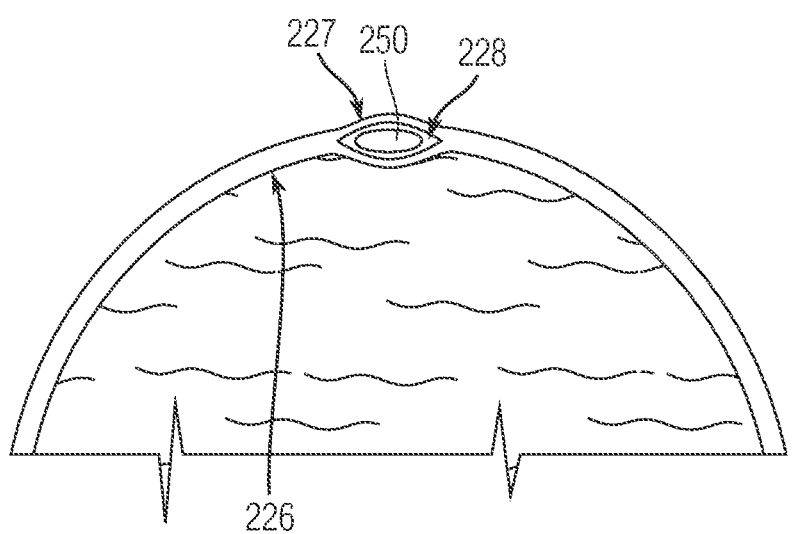
FIG. 7 is a high level diagram illustrating an exemplary configuration of an intragastric balloon device of the electro-physiologically active transducer intragastric balloon system of FIG. 2 according to one or more embodiments of the invention.

In some implementations, the stimulation unit 250 can also be disposed within the cavity and uncoupled to the shell 225 such that it can move freely within the cavity (e.g. is free floating in the fluid or gaseous medium 240 that fills the cavity 230), for instance, as shown in FIG. 6, which is a cut-away side-view of the IG balloon 200 in accordance with one or more of the disclosed embodiments. In accordance with the present embodiment, an external charging coupler would consist, in part, of a sufficiently strong magnet to reorient the free-floating acoustic generator and/or its power source to align in accordance with the correct orientation so as to facilitate inductive charging. Alternatively, or in conjunction with the foregoing, a positioning sensor within the stimulation unit 250 would communicate with an external device to instruct the user as to the optimal body position (e.g. standing, sitting, reclining, left lateral decubitus, right lateral decubitus, etc.) to obtain maximal charge coupling and/or communication with the external device.

By way of further example, in accordance with one or more of the disclosed embodiments, the stimulation unit 250 can be completely or partially encased within the shell 225. For instance, FIG. 7, which is a cut-away side-view of a section of the shell 225 of a balloon in accordance with embodiments of the present invention, depicts an inner surface 226 and opposing outer surface 227 of the shell, as well as a separation in the inner and outer layers of the shell to define a pocket 228 within which the stimulation unit 250 (or a component thereof) can be disposed such that the stimulation unit 250 is encased within the shell. In addition or alternatively, the stimulation unit 250 can be partially encased in the shell such that one or more surfaces of the stimulation unit 250 are exposed through the inner surface 226 and/or the outer surface 227 of the shell. Partial exposure of the transducer through the interior 226 or exterior surface 227 of the shell 225 can achieve practical benefits, for example and without limitation, facilitate the transmission of stimulation signals to receptors of the stomach through the medium 240, facilitate the transmission of stimulation directly to the receptors (e.g., without transmission through the medium), facilitate transmission of electronic communications to the mobile device 260, facilitate inductive charging of the stimulation unit and the like, as further described herein.

It should be appreciated that the foregoing systems and methods for operatively combining the stimulation unit 250 and the IG balloon component 205 of the improved IG balloon 200 are provided as non-limiting examples. Alternative conventions can be implemented without departing from the scope of the disclosed embodiments. For instance, the stimulation unit can be tethered to the shell using a flexible tether such that it only moves freely within a certain region of the cavity. By way of further example, the stimulation unit can be supported within the cavity at a relatively consistent position (e.g., within a central region of the cavity) by connecting the stimulation unit to one or more sides of the shell using one or more support structures. By way of further example, the stimulation unit can be integrated at various locations about the shell 225.

In some implementations, the components of the stimulation unit 250 can be sealed in a single housing or enclosure 255. The housing can take any number of sizes and shapes. For example and without limitation, the housing can have a cylindrical, spherical, oblong, conical, rectangular shape. Preferably, the size of the housing is suitable for insertion along with the IG balloon 205 through the patient's mouth and esophagus and into the stomach 50. For instance, the housing, can be integrated with the IG balloon such that it and the shell 225 can be folded or rolled up in a sleeve that can be passed down the esophagus into the patient's stomach. In such a configuration, the sleeve can be configured to rupture once enough saline is infused into the internal cavity 230 via the long fill tube, thereby allowing the shell to inflate and transition the IG balloon 205 into an operative state.

Figure 8:
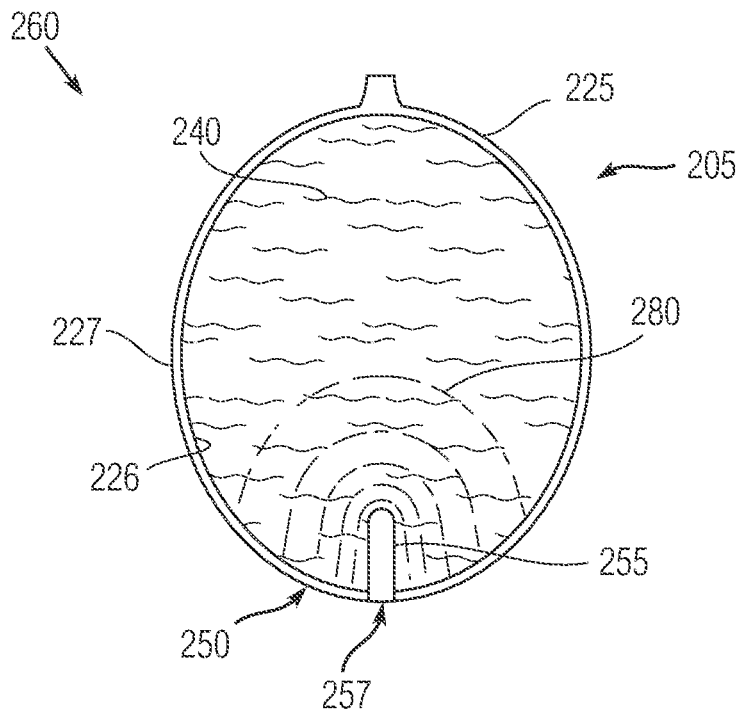
FIG. 8 is a diagram illustrating an exemplary configuration of an intragastric balloon device of the electro-physiologically active transducer intragastric balloon system of FIG. 2 in which the stimulation device has a bullet shaped housing according to one or more embodiments of the invention.

The shape of the housing 255 and its manner of integration with the IG balloon 205 can be defined to facilitate insertion, as well as to facilitate operation of the stimulation unit 250 after deployment. More specifically, the shape of the housing is not necessarily spherical can be defined to optimize the ability of the transducer to transmit mechanical waves through the fluid or gas within the cavity 230. For instance, as shown in FIG. 8, the stimulation device can have a bullet shaped housing 255 to facilitate multi-directional propagation of stimulation waves 280 through the medium 240. By way of further example, as also shown in FIG. 8, the stimulation unit 250 can be attached toward an end of the IG balloon 205 (e.g., near its base end opposite from the fill valve) with a length of the housing 255 extending inward toward the center of the cavity of the balloon such that the stimulation waves radiate away from the bottom end throughout the medium. By way of further example, as shown in FIG. 2E, the stimulation unit 250 can be free floating so as to facilitate transmission of signals through the medium in all directions about the stimulation unit.

As noted, in accordance with some embodiments, the housing 255 can be configured to traverse through the wall or the shell of the balloon, such that the signal generating component extends within the cavity and a portion of the stimulation unit housing lies at the outer surface of the shell. For example, FIG. 8, illustrates an exemplary configuration in which a generally flat end 257 of a bullet shaped housing 255 is exposed through the outer surface 227 of the shell 225. Such a configuration can, for example, provide the advantage of better reception for wireless communication signals, more efficient transcutaneous inductive charging of the stimulation unit and, optionally, can expose sensors to the environment within the stomach.

Figure 9:
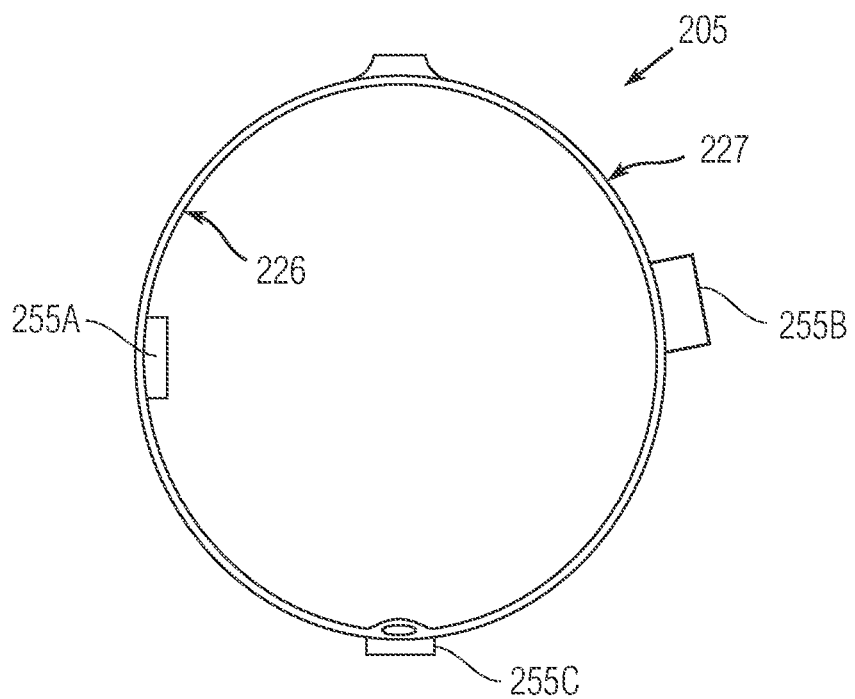
FIG. 9 is a diagram illustrating an exemplary configuration of an intragastric balloon device of the electro-physiologically active transducer intragastric balloon system of FIG. 2 that contains multiple impulse generators according to one or more embodiments of the invention.

Although the exemplary embodiments of the EAT system 200 described herein comprise a single stimulation unit 250 with components included within a single housing 255, the EAT 200 can also include multiple stimulation units disposed at respective positions on or within the shell 225 or within the cavity 230. Similarly, a given stimulation unit 250 can comprise multiple separate components that are disposed at respective locations on or within the IG balloon 205. For example, as shown in FIG. 9, the stimulation unit 250 may comprise two separate impulse generators sealed in respective housings 255A and 255B, wherein housing 255A is coupled to the interior surface 226 of the shell 225 at one side of the IG balloon 205 and the other 255B coupled to the outer surface 227 of the shell at an opposite side of the balloon. In addition, the two impulse components can be in electronic communication (e.g., by wired or wireless connection) with control circuitry sealed within a housing 255C that is encased within the shell 225 and that is configured to remotely coordinate the operation of the devices in housing 255A and 255B over a wired or wireless electronic communication connection, as further described herein. In accordance with the foregoing, it can be further appreciated that a given discrete unit housing one or more components of a stimulation unit can be sized, shaped and positioned relative to the shell 225 to facilitate insertion as well as to facilitate its respective operation as part of the EAT system 200. In a multi-unit configuration, a sensor would determine which unit achieve best interface with the external coupling unit, such as the charging unit or the data unit, and selectively choose which unit to activate and which to deactivate, either automatically or by external selection by the user.

The features and functionality of the stimulation unit 250 will be further appreciated with reference to FIG. 10, which is a block system diagram illustrating an exemplary configuration of the stimulation unit 250 in accordance with one or more embodiments of the invention.

As shown and further described herein, the stimulation unit 250 can be provided within a sealed housing 302. The stimulation unit can comprise a control circuit 305 that operatively connects various hardware and software components that serve to enable operation of the stimulation unit. As shown, the stimulation unit can include a processor 310, one or more signal generating units 315 ("transducer" 315) and a power supply 325. In some implementations, the stimulation unit can also include a communication interface 350. Accordingly, using the communication interface, the processor can convey information to one or more devices that are external to the stimulation unit 250, such as another stimulation unit or an external computing device, such as a mobile device 260. The stimulation unit can also include one or more computer readable storage mediums, for instance, a memory 320 and/or a storage medium 390A.

More specifically, the processor 310 serves to execute software instructions that configure the processor to coordinate operation of the stimulation unit 250, as further described herein. The processor 310 can be a number of processors, a multi-processor core, or some other type of processor, depending on the particular implementation. In a basic configuration, the processor controls the operation of the transducer 315 and causes the transducer to transmit signals suitable for transmission through the medium and, more generally, for stimulating various stomach receptors.

The transducer 315 can be any variety of transducers that are suitable for transferring energy in the form of mechanical and/or acoustic signals directly into the medium or indirectly through the shell 325 such that the energy of the signal thereafter travels (e.g., radiates or propagates) in one or more directions through the medium, for instance, in the form of mechanical waves radiating outward from the point of origin. In a more basic implementation, the transducer can be an electro-mechanical device configured to controllably move (e.g., vibrate or shake in one or more directions) so as to generate one or more mechanical pulses or waves.

In addition or alternatively, the transducer can be an acoustic transducer. In the following description, the term "acoustic" is to be construed broadly to include mechanical and acoustic signals, for example, acoustic signals in a frequency range of 10 Hz to 50 MHz and, more optionally, in the 1200-2000 Hz range. In some implementations, however, signals having lower or higher frequencies can be used. Preferably, the wavelength, frequency and intensity of a sonic impulse imparted by the transducer 315 is strong enough to achieve maximum effectiveness and can vary from patient to patient and can be dynamically controlled and adjusted during use, as necessary.

In some configurations the transducer 315 can be configured to introduce the stimulation signals such that they propagate through the medium 240 in one or more directions and through the thickness of the shell 225, so as to stimulate the stomach receptors R that are adjacent to or in the vicinity of the IG balloon 205. In addition or alternatively, the signals can also propagate circumferentially along or within the outer shell 225. It should also be understood that stomach receptors are not required to be directly touching the shell 225 to achieve stimulation. The energy of a signal can similarly propagate from the shell through the stomach contents separating the shell from receptors at nearby stomach wall surfaces (e.g., air, stomach contents, stomach lining etc. that separates receptors R from the shell 225). In an alternative configuration, a medium other than saline solution might be used to inflate the balloon, such that the propagation of acoustic waves is preferable to that through water or saline solution, e.g., gas such as air or nitrogen.

In some implementations, the transducer 315 can be configured to generate stimulation signals having certain properties or parameters. The properties of the signals can be defined by the specific hardware configuration of the transducer and, in addition or alternatively, controlled using the processor 310. Signal properties that can be defined and adjusted to more effectively stimulate the stomach receptors can include, for example without limitation, specific frequencies or ranges of frequencies, specific signal intensities or ranges of intensities, specific waveforms, specific patterns in which signals are administered and any combination of the foregoing parameters. Moreover, although the transducer can be configured to transmit a signal comprising individual impulses/pulses, the transducer can also be configured to generate a stream of pulses or waves having a particular frequency, period, shape, wavelength, pattern, amplitude and the like. It should be understood that these and other signal characteristics and administration patterns can be selected and modified either prior to or dynamically during treatment in the methods and systems herein.

The communication interface 350 can be any interface that enables communication between the processor 310 and external devices as would be understood in the art. Preferably, the communication interface includes, but is not limited to an integrated wireless network interface, a radio frequency transmitter/receiver (e.g., Bluetooth, cellular, NFC) and/or any other such interfaces for connecting the processor to other computing devices like mobile device 260 and/or communication networks, such as private networks and the Internet. Such connections can include, preferably, a wireless connection (e.g., using the IEEE 802.11 standard), though it should be understood that communication interface can comprise any interface that enables communication to/from the processor. Communication interface can also be configured to facilitate wireless communication between various components of the stimulation unit 250, for instance, wireless transmission of stimulation control signals from the processor to a physically separate transducer 315.

Optionally, the stimulation unit 250 can include one or more sensors 340 that are used to measure various conditions within and/or outside of the IG balloon 205. For instance, sensor 340 can comprise a pressure sensor configured to measure the pressure of the stomach and the measured pressure value can be monitored as a measure of stomach fullness. Sensor leads can further be exposed outside of the IG balloon's cavity (e.g., exposed to the surrounding area of the stomach so as to take direct measurements) although alternative sensor locations can be envisioned without departing from the scope of the disclosed embodiments.

The power supply 325, can be any style of energy storage device as would be understood by those in the art of implantable medical devices. The power supply can be coupled to the processor 310 and other components of the stimulation unit requiring energy/power for operation. For example and without limitation, the power supply can be a rechargeable power source, such as a Lithium-ion battery. The power supply can be rechargeable using transcutaneously received signals from an external source. Such signals can include electromagnetic signals (e.g., RF signals) as well as magnetic signals (e.g., inductive signals). Accordingly, the power supply 325 can incorporate a receiver (e.g., coil or antenna) to receive such signals and/or a transmitter to transmit signals to an external receiver. To provide continuous operation for extended periods of time, the power supply can have a capacity suitable for periodic, intermittent or continuous operation of the processor, the transducer and other electronic components of the stimulation unit, as necessary given the particular mode and frequency of operation. It can be appreciated that different components that can be used in the stimulation unit 250, such as different types of transducers, may result in different power requirements. Accordingly, capacity of the power supply and its recharging capacity may be selected in accordance with needs of a particular system. It can be further appreciated that power supply 325 can comprise multiple individual power supply units, for instance, a dedicated power supply can be provided to power the transducer, while the remaining control electronics can be powered by a separate power supply.

The processor can also be operatively connected to a computer readable memory 320 and/or a storage medium 390A, thereby enabling the processor to receive and execute instructions stored on the memory and/or on the storage. The memory 320 can be, for example, a random access memory (RAM) or any other suitable volatile or non-volatile computer readable storage medium. In addition, the memory 320 can be fixed or removable.

The storage can take various forms, depending on the particular implementation. For example, the storage can comprise one or more components or devices such as a hard drive, a volatile or non-volatile flash memory or some combination of the above. As shown in FIG. 10, the storage can be local storage 390A, which is on board the stimulation device 250. In addition or alternatively the storage can be a remote storage medium located on an external computing device, such as device storage 390B provided on-board the smartphone 260. In addition or alternatively, storage can be a remote storage system such as a cloud based data storage system 390C.

In some implementations, one or more software modules 330 are encoded in the memory 320 and/or the storage 390A. The software modules 330 can comprise one or more software programs or applications having computer program code, a script, or a set of interpretable instructions executed in the processor 310. Such computer program code or instructions for carrying out operations and implementing aspects of the systems and methods disclosed herein can be written in any combination of one or more programming languages or scripts. Preferably, included among the software modules 330 is a stimulation control module 332, a stimulation programming module 334, a communication module 334, a data analysis and storage module 338. During execution of the stimulation control module 332, the processor can be configured to execute various stimulation regimens using the transducer(s) 315 to stimulate receptors in the stomach, as will be described in greater detail below. During execution of the stimulation programming module 334, the processor can be configured to generate treatment programs including stimulation regimens and define or adjust control parameters so as to tailor the treatment of the patient to dynamically changing conditions. During execution of the communication module 334, the processor can be configured to, using the communication interface 350, communicate with various components of the stimulation unit and wirelessly connected computing devices such as the mobile device 260. During execution of the data analysis and storage module 338, the processor can be configured to, capture, store and analyze various data elements relating to the treatment of the patient, as will be described in greater detail below.

In some implementations, the program code can execute entirely on the stimulation unit 250, as a stand-alone software package, partly on the stimulation unit and partly on one or more remote computer/device (e.g., mobile device 260 and/or a remote computing system) or entirely on one or more remote computers/devices. In the latter two embodiments, the remote computer systems can be operatively connected to the stimulation unit processor 310 through any type of electronic data connection or network, including a local area network (LAN) or a wide area network (WAN), or the connection can be made through an external computer (for example, through the Internet using an Internet Service Provider).

It can also be said that the program code of the software modules 330 and one or more of the non-transitory computer readable storage devices (such as the memory 320 and/or the storage 390A) form a computer program product that can be manufactured and/or distributed in accordance with the present disclosure, as is known to those of ordinary skill in the art. It should be understood that in some illustrative embodiments, one or more of the software modules 330 can be downloaded by a device (e.g., the stimulation unit processor 310 and/or the mobile device processor, not shown) over a communications network (not shown) from another device or system for use within the system 100.

In addition, it should be noted that other information and/or data relevant to the operation of the EAT system 200 and methods can also be stored on storage 390A and/or in memory 320. For instance, the stored data items and elements can include, but are not limited to a patient profile, pre-defined stimulation programs, control parameters that define aspects of the stimulation treatment, encoded instructions or programs that are used to coordinate the operation of various stimulation device components (e.g., the transducer 315, the communication interface 350 and the like), patient-specific settings and parameters that further define aspects of the stimulation operations, and the like. It should be further appreciated that although such information can be stored locally at the on-board storage or memory of the stimulation unit 250, in certain implementations, any of the data elements can be stored remotely (e.g., on mobile device storage 360B or remote storage 360C) and made accessible to the processor 310 over a communication connection. Similarly, such information can be processed and utilized to administer stimulation using the stimulation unit 250 through coordinated operation of the stimulation unit 250 and one or more of the remote devices such as the mobile device 260.

As noted, in some implementations, a mobile device 260 can be integrated into the EAT system 200 and facilitates administration of the obesity treatment regimen using the EAT system through coordinated operation of the stimulation unit 250 and the mobile device 260, which are in wireless communication with one another. According to various embodiments, the mobile device 260 can be any mobile computing and/or data processing apparatus capable of embodying the systems and/or methods described herein, including, but not limited to, a personal computer, tablet computer, personal digital assistant, mobile electronic device, a wearable electronic device, a cellular telephone, or a smart phone device.

In order to facilitate operation of the EAT system 200, the mobile device also preferably includes a user interface and a display that, as would be understood in the art of electronic computing devices, serves to facilitate the output of information to users and the capture of information. In the particular implementation shown in FIGS. 2 and 10, the user interface and display can be integrated into a touchscreen 370. The touchscreen serves to facilitate the capture of information about the patient and the treatment, such as patient information, doctor information, patient or doctor defined settings, information about the patient's day-to day activity during treatment, and the like. Interface also serves to facilitate the capture of commands from the user such as an on-off commands or settings related to operation of the EAT system 200.

The mobile device 260 according to certain embodiments executes instructions in the form of one or more software modules that configure the mobile device to communicate and interface with the stimulation unit 250, thereby preferably initiating, facilitating, maintaining, and/or enhancing the operation of the EAT system 200. In particular, the mobile device can be provided with a patient application module that, when executed by the mobile device's processor (not shown), configures the mobile device to, for example and without limitation: guide a patient to input information pertinent to the patient's health and treatment; store information received from the stimulation unit; monitor the patient's activity using one or more on-board sensors or devices in communication with the mobile device, such as, health and fitness monitoring devices; process the received information, settings and instructions to define treatment programs and stimulation regimens that can be implemented using the stimulation unit; communicate received instructions and stimulation programs to the stimulation unit 250 thereby enabling the stimulation device to perform the stimulation operations; store, monitor and output information relating to the patient's health and treatment to the patient via the display or a portal that is accessible to the user or a healthcare professional participating in the patient's treatment.

The patient application can comprise a stand-alone software application executing on the mobile device 260 or, certain features and functionality of the patient application module can be executing partially on one or more other computing devices that are accessible by the mobile device over a communication network (not shown). Similarly, the mobile device executing the patient application can be used to perform one or more of the operations described herein as being performed by the stimulation unit 250.

It should be noted that while FIGS. 2 and 10 depicts the EAT system 200 with respect to a single mobile device 260, any number of such devices can interact with the system in the manner described herein. It should also be noted that while the system is further described as being interacted with by a patient and/or a healthcare professional, any number of such users can interact with the system in the manner described herein. For instance, a healthcare professional can access and monitor information relating to the operation of the EAT system 200 from a remote computing device (not shown) and define operational settings and treatment parameters from the remote computer that are received or downloaded and implemented by the mobile device 260 and/or the stimulation unit 250, say, from the remote storage 390C.

It should be further understood that while the various computing devices and machines referenced herein, including but not limited to mobile device 260 and the stimulation unit 250, are referred to herein as individual/single devices and/or machines, in certain implementations the referenced devices and machines, and their associated and/or accompanying operations, features, and/or functionalities can be combined or arranged or otherwise employed across any number of such devices and/or machines, such as over a network connection, a wired or wireless communication connection, as is known to those of skill in the art.

The operation of the electro-physiologically active transducer intragastric balloon system 200 will be further appreciated with reference to FIG. 11 and with continued reference to FIGS. 2 and 10. FIG. 11 is a high-level flow diagram illustrating an exemplary routine 400 for administering stimulation using the stimulation unit 250 according to embodiments of the invention.

The routine 400 includes step 405 in which the EAT system 200 and the treatment program to be implemented by the EAT system is configured. As would be understood, the configuration/set-up process can include loading the patient application into the patient's mobile device 260, pairing the mobile device 260 with the stimulation unit 250, establishing the necessary permissions and logical associations between the various computing devices that are used to facilitate operation of the EAT system 200.

More specifically, the mobile device 260 executing the patient application can be configured to collect pertinent information relating to the patient and the patient's treatment, as well as store such information in a patient profile stored in one or more storage mediums. For example, the patient application can prompt the patient to input personal information via the mobile device touchscreen 370. In addition or alternatively, patient data and treatment details can be obtained in other ways, such as, through electronic access to information stored on another device (e.g., by accessing an existing patient profile including patient information input by the patient's doctor and stored on remote cloud-storage 390C). Information relating to the patient profile can be stored, for example, on local storage 390B of the mobile device, local storage of the stimulation device 390A, remote storage 390C, and any combination of one or more of the foregoing.

The set-up process can also include generating a treatment program for the patient. Moreover, any information about the treatment program that is necessary to administer treatment using the stimulation device 250 can also be loaded into the storage or memory of the devices used to implement the treatment program such as the stimulation device and/or the mobile device 260.

In some implementations, the treatment program for a patient can include one or more stimulation regimens that are executed over the course of the treatment. A stimulation regimen can include parameters according to which the stimulation unit processor 310 using the transducer 315 generates stimulation signals having specific properties. As noted, signal properties that can be controllably defined include the overall form of the stimulation signal, including for example and without limitation, an impulse, a sequence of pulses having, a pattern of the pulses (e.g., a relative timing of the pulses, time between pulses, a frequency of the pulses, a number of pulses, a total duration etc.). The properties of individual pulses can also be controllably defined, for instance, a frequency, amplitude, wavelength, period, wave shape and the like.

The stimulation program can also specify one or more pre-defined conditions that trigger the stimulation unit 250 to begin and/or cease administering stimulation using the transducer 315 according to one or more stimulation regimens. More specifically, the stimulation unit processor 310 and/or the mobile device 260, can be configured to detect the occurrence of events (e.g., through periodic, intermittent or continuous monitoring) that meet the one or more pre-defined condition(s) associated with respective stimulation regimens. Accordingly, if it is determined that the one or more conditions associated with a particular stimulation regimen are met, the processor 310 can be triggered to commence or stop executing the particular regimen accordingly. Additionally, the external monitoring device, such as a smartphone or other mobile device, may be configured to communicate with the patient via intermittent reminders and cues during to assess levels of satiety, wellness and desire to eat, processing this data to accordingly activate or deactivate the stimulation unit.

In some implementations, the triggering conditions can be user inputs, for instance, start-stop commands input by a user (e.g., as input by the patient at the mobile device 260 or a healthcare professional at a respective computer terminal) and that are transmitted wirelessly to the stimulation unit processor 310 via the communication interface 350. In addition or alternatively, the triggering conditions can comprise one or more behavioral or environmental conditions detected using the stimulation device 250 and/or the associated mobile device 260. For instance, the processor 310 can be configured for executing one or more of the software modules 330, for example, the analysis module, to use one or more of the sensors 340 to periodically measure the internal pressure within the patient's stomach and determine whether the measured pressure exceeds a prescribed threshold pressure (e.g., indicating a triggering condition of the patient eating and the stomach being at a given capacity). Triggering conditions can concern various other determinable parameters such as a time of day, a typical time that the patient eats meals, and various other environmental conditions and patient physiological and behavioral characteristics.

In addition or alternatively, the triggering conditions can be based on objective or subjective patient-data such as feedback received from the patient during use of the EAT system 200 (e.g., the patient's perception of hunger or lack thereof, emotional distress, hormonal factors, menstrual periods, depression, anxiety and the like). In addition, triggering conditions can be based on physiological data of the patient gathered by the mobile device 260 and associated health and fitness monitoring devices.

Moreover, the start/stop triggering of a stimulation regimen can be conditioned upon previously recorded or future events in the treatment program, for instance, an elapsed time since the previous stimulation treatment, the type of the previous stimulation treatment (e.g., the previously administered stimulation regimen), a scheduled upcoming stimulation regimen, the total duration of the patient's treatment using the EAT system 200, and the like. It should be understood that the foregoing triggering conditions, and the related information that is monitored and processed to selectively control application of stimulation using the EAT system 200, are provided as non-limiting examples.

Any of the aforementioned aspects of the stimulation program (e.g., triggering conditions/events, control parameters and stimulation signal parameters) can be pre-defined automatically by the EAT system 200, by the patient, by a healthcare professional and any combination of the foregoing. In addition or alternatively, the EAT system 200 (e.g., using the processor 310 and/or the mobile device 260) can be configured to define or update various parameters dynamically during operation of the EAT system 200 (e.g., using the processor 310, and mobile device 260).

More specifically, in some implementations, a pre-defined treatment program can comprise a default program that is generally applicable to multiple patients and without regard to patient-specific parameters. In addition or alternatively, various parameters of the one or more stimulation regimens can be pre-defined based on a particular patient's physical condition, habits and other such information that can be stored in the patient's profile. Moreover, various conditions and parameters associated with a stimulation program can be defined or updated dynamically based on the information recorded and measured in an ongoing basis during operation of the EAT system 200.

For instance, as noted, during set-up the mobile device 260 executing the patient application can prompt the patient and/or his healthcare provider to input information relating to the patient's physical condition, personal habits, preferences, baseline settings and the like for storage in a patient profile. The patient-specific information can be used by the mobile device 260 to define one or more initial stimulation regimens for the patient. It should be appreciated that, in addition or alternatively, one or more of the stimulation regimens can be specifically defined by the patient's doctor, for instance at the doctor's personal computing device (not shown) and then downloaded to the storage of the mobile device 260 and/or to the stimulation unit 250. The unit may also be programmed to enter a "sleep mode" during exercise or patient sleep hours, in order to conserve battery life. An accelerometer or similar component can communicate activity and positional data to achieve such selective activation and to re-enter an "active state" when certain parameters are met.

Similarly, any of the stimulation regimens and related settings can be periodically updated during use of the EAT system 200. The updates can be generated automatically by the mobile device 260 and/or the stimulation unit 250, manually by the patient or healthcare provider, or a combination of the foregoing. For instance, the stimulation unit processor 310 executing one or more of the software modules 330 including, preferably, the stimulation programming module 334 and the data analysis/storage module 338, can be configured to adjust one or more of the stimulation regimens as the IG balloon remains in position over time, say, by increasing the frequency or signal intensity that a stimulation sequence is administered, increasing the intensity of the stimulation sequence or any other pertinent parameters or triggering conditions necessary to provide the patient with a suitable level of satiety in view of the prolonged use of the IG balloon.

At step 410, the integrated IG balloon 205 and stimulation unit 250 of the EAT system 200 are physically deployed in the patient's stomach and the transitioned into an operative state. For instance, the integrated IG balloon and stimulation unit can be inserted into the patients stomach in manner conventionally used to deploy and inflate IG balloon devices, as described above. It should also be understood that the stimulation unit 250 can be activated before, during or after deployment so as to enable the stimulation unit 250 to administer stimulation and allow for calibration in each individual patient.

At step 415, the stimulation unit 250, selectively generates signals for stimulating nearby sensory receptors of the stomach according to the treatment program. More specifically, as noted, the stimulation unit's processor 310, which is configured by executing one or more of the software modules 330, including, preferably, the stimulation control module 332, can cause the transducer 315 to transmit stimulation signals suitable for activating and/or inhibiting vagal nerve activity. For instance, some of the stimulation signals transmitted using the transducer 315 can be inhibitory, whereas some can be stimulatory, as the vagus nerve has both afferent and efferent fibers.

In connection with the administration of stimulation according to the treatment program, at step 420, the stimulation unit processor 310 executing one or more of the software modules 330, including, preferably, the communication module 336, can be configured to transmit information relating to the therapy to the mobile device 260 using the communication interface 350.

As noted, this treatment information can be transmitted for storage in the patient profile as well as for further analysis and processing. For example and without limitation, the mobile device can record in local or remote storage the start and stop time of each stimulation treatment, the length of the treatment, the particular stimulation regimen applied, any sensor readings captured before, during or after the treatment and other related information. Similarly, the mobile device executing the patient application can be configured to prompt the patient to provide subjective feedback relating to the treatment and other information (e.g., information about the user's activity during the treatment, the caloric intake if food was ingested, etc.). In addition, the mobile device can be configured to notify the user the operative status of the stimulation unit (e.g., by generating an alert that the stimulation unit has been activated and/or deactivated). Similarly, the mobile device can also be configured to provide the patient with access to more detailed information about the treatment program, either in near-real time or on-demand, as well as other information relating to the settings of the EAT system 200, stimulation regimens and other treatment and health related information to the patient.

In accordance with certain embodiments, the device can also be configured according to certain implementations to offer feedback to the patient via a smartphone, watch or other connected device, which will provide incentive to interact with the EAT unit and take action based on biofeedback. Biofeedback induced action which is a well established and well proven method of psychological intervention in multiple addictive disorders, specifically in eating disorders. Provision of "wellness checks" and "weight control affirmations" as an adjunct to the physiologic intervention provided by the EAT system may further augment its usefulness. Further, intermittent and unscheduled positive messages, such as wellness, projected clothing size, upcoming trips to vacation spots, life expectancy projections, messages of pride and self confidence, suggestions to increase exercise, ingest additional fluids, etc., may further be provided by the software operating on the connected device.

In some implementations, the patient profile can be also be provided to the patient or healthcare provider, e.g., through a web-based portal. The portal can include, but is not limited to, the patient application executing on a user's computing device or a web-based portal that is accessible through the internet. The computing devices of the EAT system 200 can also be configured to integrate the stored information (e.g., the patient profile) with other dietary, health and exercise activity logs so as to build a more comprehensive log of the patient's physical health and progress over time. The diet, health and workout activity information can be input into the portal either manually by the patient or automatically by a device that gathers physical activity data such as a pedometer and other such health and fitness trackers. Accordingly, the computing systems of the EAT system and users thereof can further leverage such information in defining and tailoring the treatment program, including without limitation, the stimulation regimens and conditions triggering the administration of stimulation by the stimulation device 250.

At step 425, the EAT system monitors for the occurrence of one or more triggering conditions. As noted, the stimulation unit processor 310 executing one or more software modules 330 (e.g., the data analysis/storage module 338) and/or the mobile device 260, which is executing the patient application, can be configured to intermittently, periodically or continuously monitor the occurrence of various triggering conditions, which can prompt the stimulation unit to selectively start or stop application of stimulation. Similarly at step 430, the stimulation unit 250 and/or the mobile device 260 can be configured to intermittently or periodically analyze the data collected and stored relating to the ongoing treatment of the patient using the EAT system 200 so as to dynamically adjust the treatment program as noted (e.g., re-configure the EAT system as discussed in relation to step 405, for example).

FIGS. 1 through 12 are conceptual illustrations allowing for an explanation of the present invention. Those of skill in the art should understand that various aspects of the embodiments of the present invention could be implemented in hardware, firmware, software, or combinations thereof. In such embodiments, the various components and/or steps would be implemented in hardware, firmware, and/or software to perform the functions of the present invention. That is, the same piece of hardware, firmware, or module of software could perform one or more of the illustrated blocks (e.g., components or steps).

In software implementations, computer software (e.g., programs or other instructions) and/or data is stored on a machine-readable medium as part of a computer program product, and is loaded into a computer system or other device or machine via a removable storage drive, hard drive, or communications interface. Computer programs (also called computer control logic or computer readable program code) are stored in a main and/or secondary memory, and executed by one or more processors (controllers, or the like) to cause the one or more processors to perform the functions of the invention as described herein. In this document, the terms "machine readable medium," "computer program medium" and "computer usable medium" are used to generally refer to media such as a random access memory (RAM); a read only memory (ROM); a removable storage unit (e.g., a magnetic or optical disc, flash memory device, or the like); a hard disk; or the like.

Notably, the figures and examples above are not meant to limit the scope of the present invention to a single embodiment, as other embodiments are possible by way of interchange of some or all of the described or illustrated elements. Moreover, where certain elements of the present invention can be partially or fully implemented using known components, only those portions of such known components that are necessary for an understanding of the present invention are described, and detailed descriptions of other portions of such known components are omitted so as not to obscure the invention. In the present specification, an embodiment showing a singular component should not necessarily be limited to other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present invention encompasses present and future known equivalents to the known components referred to herein by way of illustration.

The foregoing description of the specific embodiments will so fully reveal the general nature of the invention that others can, by applying knowledge within the skill of the relevant art(s) (including the contents of the documents cited and incorporated by reference herein), readily modify and/or adapt for various applications such specific embodiments, without undue experimentation, without departing from the general concept of the present invention. Such adaptations and modifications are therefore intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s).

While various embodiments of the present invention have been described above, it should be understood that they have been presented by way of example, and not limitation. It would be apparent to one skilled in the relevant art(s) that various changes in form and detail could be made therein without departing from the spirit and scope of the invention. Thus, the present invention should not be limited by any of the above-described exemplary embodiments, but should be defined only in accordance with the following claims and their equivalents.

I claim:

1. A method for treating obesity through the use of an electro-physiologically active transducer intragastric balloon device, the method comprising:
    deploying an intragastric balloon ("IG balloon") within a stomach of a patient, the IG balloon having a shell surrounding an internal volume for containing a medium therein;
    generating a stimulation signal by a stimulation unit integrated into the IG balloon; and
    transmitting the stimulation signal through the medium to stimulate one or more sensory receptors in the stomach of the patient.

2. The method of claim 1 wherein generating the stimulation signal comprises generating theft stimulation signal by a transducer that is in communication with the stimulation unit.

3. The method of claim 1 wherein transmitting the stimulation signal through the medium comprises transmitting the stimulation signal through a fluid or gaseous medium.

* * * * *